United States Patent
Denard et al.

(10) Patent No.: US 12,402,926 B2
(45) Date of Patent: Sep. 2, 2025

(54) SYSTEM AND METHOD FOR PROVIDING A BONE CERCLAGE

(71) Applicant: ARTHREX, INC., Naples, FL (US)

(72) Inventors: Patrick Joel Denard, Jacksonville, OR (US); Peter Dreyfuss, Naples, FL (US); Steven William Rolenc, Naples, FL (US); Andrew Christian Petry, Naples, FL (US)

(73) Assignee: ARTHREX, INC., Naples, FL (US)

( * ) Notice: Subject to any disclaimer, the term of this patent is extended or adjusted under 35 U.S.C. 154(b) by 606 days.

(21) Appl. No.: 17/186,173

(22) Filed: Feb. 26, 2021

(65) Prior Publication Data

US 2022/0273349 A1     Sep. 1, 2022

(51) Int. Cl.
| | | |
|---|---|---|
| *A61B 17/82* | (2006.01) | |
| *A61B 17/04* | (2006.01) | |
| *A61B 17/88* | (2006.01) | |

(52) U.S. Cl.
CPC .......... *A61B 17/82* (2013.01); *A61B 17/0469* (2013.01); *A61B 17/8861* (2013.01)

(58) Field of Classification Search
CPC .. A61B 17/82; A61B 17/0469; A61B 17/8861
See application file for complete search history.

(56) References Cited

U.S. PATENT DOCUMENTS

| | | |
|---|---|---|
| 3,111,945 A | 11/1963 | Von Solbrig |
| 3,469,573 A | 9/1969 | Florio |
| 4,008,912 A | 2/1977 | Kotov |
| 4,119,091 A | 10/1978 | Partridge |
| 4,146,022 A | 3/1979 | Johnson et al. |
| 4,606,335 A | 8/1986 | Wedeen |
| 4,643,178 A | 2/1987 | Nastari et al. |
| 4,667,662 A | 5/1987 | Titone et al. |
| 5,012,818 A | 5/1991 | Joishy |
| 5,190,545 A | 3/1993 | Corsi et al. |
| 5,250,053 A | 10/1993 | Snyder |
| 5,318,566 A | 6/1994 | Miller |
| 5,415,658 A | 5/1995 | Kilpela et al. |
| 5,454,821 A | 10/1995 | Harm et al. |
| 5,462,542 A | 10/1995 | Alesi, Jr. |
| 5,501,688 A | 3/1996 | Whiteside et al. |
| 5,540,703 A | 7/1996 | Barker, Jr. et al. |
| 5,573,286 A | 11/1996 | Rogozinski |

(Continued)

FOREIGN PATENT DOCUMENTS

WO     2015009808 A1     1/2015

OTHER PUBLICATIONS

International Preliminary Report on Patentability for International Application No. PCT/US2017/014924 mailed Sep. 27, 2018.

(Continued)

*Primary Examiner* — Sameh R Boles
(74) *Attorney, Agent, or Firm* — Carlson, Gaskey & Olds, P.C.

(57) ABSTRACT

A system for providing a bone cerclage according to an exemplary aspect of the present disclosure includes, among other things, a suture passer including a shaft. The shaft includes a passageway and a slot leading to the passageway. The slot has a variable width along a length of the passageway. A method is also disclosed.

20 Claims, 5 Drawing Sheets

(56) References Cited

U.S. PATENT DOCUMENTS

| | | |
|---|---|---|
| 5,573,542 A | 11/1996 | Stevens |
| 5,628,756 A | 5/1997 | Barker, Jr. et al. |
| 5,772,663 A * | 6/1998 | Whiteside .............. A61B 17/82 |
| | | 606/103 |
| 5,788,697 A | 8/1998 | Kilpela et al. |
| 5,830,234 A | 11/1998 | Wojciechowicz et al. |
| 5,851,209 A | 12/1998 | Kummer et al. |
| 5,908,421 A | 6/1999 | Beger |
| 5,997,542 A * | 12/1999 | Burke .................... A61B 17/82 |
| | | 606/907 |
| 6,093,190 A | 7/2000 | Mattchen |
| 6,302,889 B1 | 10/2001 | Keller |
| 6,368,326 B1 | 4/2002 | Dakin et al. |
| 6,475,220 B1 * | 11/2002 | Whiteside .............. A61B 17/82 |
| | | 606/224 |
| 6,610,071 B1 | 8/2003 | Cohn et al. |
| 6,716,234 B2 | 4/2004 | Grafton et al. |
| 7,207,090 B2 | 4/2007 | Mattchen |
| 7,207,993 B1 | 4/2007 | Baldwin et al. |
| 7,326,222 B2 | 2/2008 | Dreyfuss et al. |
| 8,162,997 B2 | 4/2012 | Struhl |
| 8,231,626 B2 | 7/2012 | Hulliger et al. |
| 8,298,247 B2 | 10/2012 | Sterrett et al. |
| 8,337,534 B2 | 12/2012 | Celli et al. |
| 8,460,295 B2 | 6/2013 | McClellan et al. |
| 8,574,235 B2 | 11/2013 | Stone |
| 8,672,969 B2 | 3/2014 | Stone et al. |
| 8,984,720 B2 | 3/2015 | Gephart |
| 9,826,969 B2 | 11/2017 | Larsen |
| 10,052,094 B2 | 8/2018 | Spenciner |
| 10,136,886 B2 | 11/2018 | Norton et al. |
| 10,143,506 B2 | 12/2018 | Dreyfuss et al. |
| 10,314,628 B2 | 6/2019 | Dooney et al. |
| 10,485,532 B2 * | 11/2019 | Norton ............... A61B 17/0401 |
| 2005/0033365 A1 | 2/2005 | Courage |
| 2009/0306668 A1 | 12/2009 | Dell'Oca |
| 2010/0211075 A1 | 8/2010 | Stone |
| 2010/0249853 A1 | 9/2010 | Celli et al. |
| 2011/0295279 A1 * | 12/2011 | Stone .................. A61B 17/0482 |
| | | 606/145 |
| 2012/0109129 A1 | 5/2012 | Bernstein |
| 2013/0018375 A1 | 1/2013 | Dell'Oca |
| 2013/0096612 A1 | 4/2013 | Zajac et al. |
| 2013/0239974 A1 | 9/2013 | O'Brien et al. |
| 2014/0249530 A1 | 9/2014 | Babikian et al. |
| 2014/0257377 A1 | 9/2014 | Akutsu et al. |
| 2015/0127003 A1 | 5/2015 | Songer et al. |
| 2016/0183991 A1 | 6/2016 | Pratt |
| 2017/0265917 A1 | 9/2017 | Dreyfuss et al. |
| 2017/0265918 A1 | 9/2017 | Dooney et al. |
| 2022/0000501 A1 * | 1/2022 | Tal ..................... A61B 17/0485 |

OTHER PUBLICATIONS

Y.M. Por, M.J. Lavin, "Techniques of intraocular lens suspension in the absence of capsular/zonular support", Survey of Ophthalmology, vol. 50, nr. 5, Sep.-Oct. 2005.

* cited by examiner

SYSTEM AND METHOD FOR PROVIDING A BONE CERCLAGE

TECHNICAL FIELD

This disclosure relates to a system and method for providing a bone cerclage.

BACKGROUND

Cerclages are used to maintain the relative position of fractured bone fragments or sections of cut bone to promote healing. While cerclages can be used relative to any fractured or cut bone, they are commonly used to promote healing of femoral fractures. Cerclages are also used relative to other bones such as the humerus and sternum, as examples. In the context of the sternum, the sternum is cut during some surgical procedures, such as during open heart surgery. After the procedure, a cerclage may be used to maintain the relative position of cut sections of the sternum to promote healing. Some known cerclages include materials such as cable (i.e., wire) or fabric, and are provided by wrapping the cable or fabric around a fractured or cut bone a single time. After wrapping, the cable or fabric is then locked into place relative to the bone using a plug or clip, as examples.

SUMMARY

A system for providing a bone cerclage according to an exemplary aspect of the present disclosure includes, among other things, a suture passer including a shaft. The shaft includes a passageway and a slot leading to the passageway, and the slot has a variable width along a length of the passageway.

In a further embodiment, the system includes a sheath and a strand of suture projecting from the sheath.

In a further embodiment, the sheath is more rigid than the strand of suture.

In a further embodiment, the sheath exhibits a larger diameter than the strand of suture.

In a further embodiment, the strand of suture is a first strand of suture and at least one additional strand of suture projects from the sheath.

In a further embodiment, a length of the sheath is longer than a length of the passageway.

In a further embodiment, the slot includes a first width adjacent an entrance of the passageway, the slot includes a second width along a main portion the passageway, and the first width is greater than the second width.

In a further embodiment, the first width is sized so as to permit the sheath and suture to enter the passageway via the slot, and the second width is sized so as to prevent the sheath from exiting the passageway via the slot and so as to permit suture to exit the passageway via the slot.

In a further embodiment, the slot is provided by a gap in a superior surface of the shaft.

In a further embodiment, the shaft includes a curved section, and the passageway and slot are provided at least partially in the curved section.

In a further embodiment, the suture passer includes a handle connected to the shaft, and the shaft includes a substantially straight section between the handle and the curved section.

A method for providing a bone cerclage according to an exemplary aspect of the present disclosure includes, among other things, passing a sheath and a strand of suture around a bone. The sheath is connected to the strand of suture. Further, the method includes tensioning the strand of suture to tighten the strand of suture relative to the bone, and securing the strand of suture to the bone.

In a further embodiment, the passing step includes positioning a suture passer relative to the bone, the suture passer includes a shaft, the shaft includes a passageway and a slot leading to the passageway, and the slot has a variable width along a length of the passageway.

In a further embodiment, the slot includes a first width adjacent an entrance of the passageway, the slot includes a second width along a main portion of the passageway, and the first width is greater than the second width.

In a further embodiment, the passing step includes inserting the sheath into the entrance and pushing the sheath through the passageway, and, as the sheath is pushed through the passageway, the sheath is prevented from exiting the passageway via the slot and suture is permitted to exit the passageway via the slot.

In a further embodiment, the passing step includes pushing the sheath through the passageway until a distal end of the sheath projects out an exit of the passageway, and the passing step further includes pulling the distal end of the sheath to remove the sheath from the passageway.

In a further embodiment, after the passing step, the method includes adjusting a position of the suture passer and then passing the sheath and the strand of suture around the bone another time before the securing step.

In a further embodiment, the securing step includes securing the strand of suture to the bone by tying a knot or without tying a knot.

In a further embodiment, further comprising bending a portion of a shaft based on a size of the bone before the passing step, wherein the portion is distal of an exit of a passageway.

In a further embodiment, the tensioning step includes using a tensioner to tighten the strand of suture.

The embodiments, examples and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

BRIEF DESCRIPTION OF THE DRAWINGS

FIG. 11 is another view of the suture passer and assembly arranged relative to the bone. In FIG. 11, the sheath has exited the passageway and the strand of suture has been passed around the bone.

FIG. 13 is a side view of the suture passer of FIG. 12 arranged relative to a bone. In FIG. 13, the bendable section is bent relative to its position in FIG. 12.

DETAILED DESCRIPTION

This disclosure details a system and method for providing a bone cerclage. The bone cerclage maintains the relative position of fractured bone fragments to promote healing. In this disclosure, the bone cerclage is provided at least partially by suture wrapped around bone at least once. In this respect, the bone cerclage may be referred to as a suture wrap cerclage.

Figure 1:
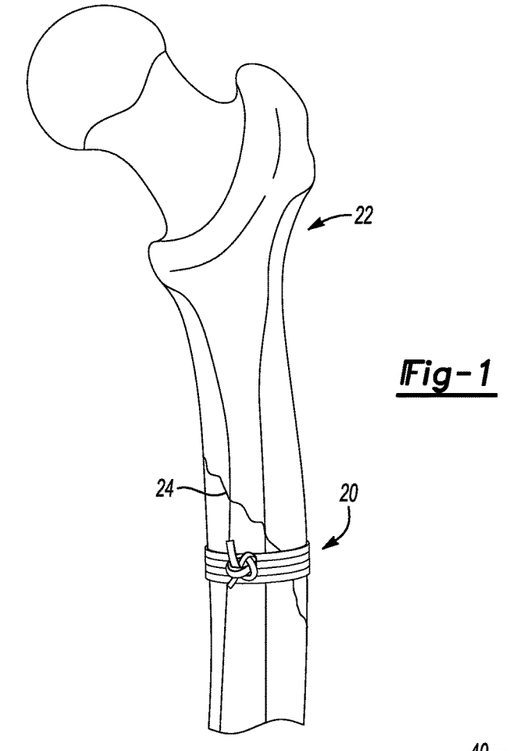
FIG. 1 illustrates a fractured bone provided with a suture wrap cerclage.

FIG. 1 illustrates a non-limiting example of a suture wrap cerclage 20 provided relative to a bone 22 with a fracture 24. In this example, the bone 22 is a femur. Femurs can fracture, for example, from a traumatic injury or as the result of an orthopedic procedure, such as a hip replacement. The suture wrap cerclage 20 fixes the fractured fragments of the bone 22 relative to one another, which promotes healing. While specific reference is made to femurs, it should be understood that this disclosure is not limited to femoral fractures, and extends to other bones, including but not limited to the humerus and the sternum. Further, this disclosure is not limited to being used relative to fractured bones and can be used to promote healing of cut bones.

In one non-limiting example of a disclosed method, a user such as a surgeon, for example, may make use of a collection of components, referred to herein as a "system." Among other things, an example system includes a suture passer 26 (FIG. 2) and an assembly 28 (FIG. 3) including a strand of suture 30 and a sheath 32.

The suture passer 26 is a device, specifically a medical device, configured to facilitate maneuvering of the assembly 28 around a bone in order to pass the strand of suture 30 around the bone such that a suture wrap cerclage can be provided adjacent a fracture, for example. With specific reference to FIG. 2, the suture passer 26 includes a handle 34 and a shaft 36 projecting distally from the handle 34. The terms "distal" and "proximal" are labeled in some figures for ease of reference.

Figure 2:
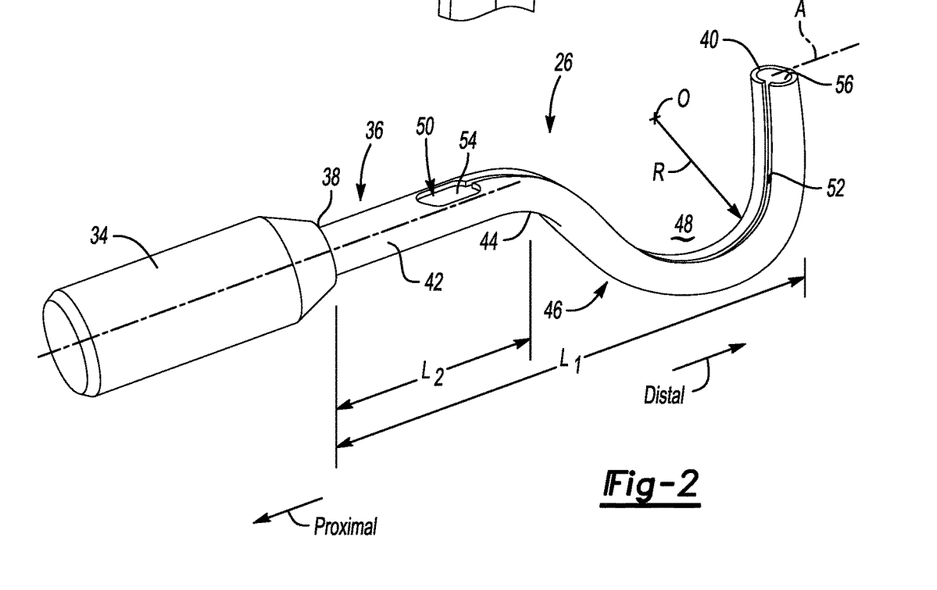
FIG. 2 is a side-perspective view of an example suture passer.

The handle 34 is configured to be grasped by a user, namely a surgeon, such that the user can maneuver the shaft 36 into a particular position. In one example, the shaft 36 is made of a metallic material and is a one-piece structure. The shaft 36 has an overall length $L_1$ between a proximal end 38 adjacent the handle 34 and a distal end 40, which is a distal-most end of the suture passer 26 in this example. The distal end 40 may be sharp or blunt. The shaft 36 includes a straight section 42 along a length $L_2$ between the proximal end 38 and a point 44 between the proximal and distal ends 38, 40. Along the straight section 42, the shaft 36 is centered around the central longitudinal axis A of the suture passer 26.

Distal of the straight section 42, the shaft 36 includes a curved section 46. The curved section 46 extends from the point 44 to the distal end 40. The curved section 46, in this example, is curved so as to follow a constant radius R having an origin O in an expected bone location 48. The origin O is spaced distally of the point 44. Beginning at the point 44, the curved section 46 initially follows the radius R by gradually extending in an inferior direction, which is a downward direction in FIG. 2, relative to the central longitudinal axis A, until the curved section 46 reaches a point directly inferior to the origin O where the radius R is perpendicular to the central longitudinal axis A. Then, following the radius R, the curved section 46 gradually extends in a superior direction opposite the inferior direction toward the central longitudinal axis A as the curved section approaches the distal end 40. The radius R in this example corresponds to the expected contour of a bone. Suture passers having differently-sized or shaped curved sections may be available to the user such that an appropriate suture passer may be selected for a particular bone size or procedure. The curved section 46 could exhibit a different shape and need not follow a constant radius.

In order to facilitate the passing of suture, the shaft 36 includes a passageway 50 and a slot 52 leading to the passageway 50. In general, the shaft 36 is partially hollow and the hollow interior of the shaft 36 provides the passageway 50. Further, the slot 52 is provided by a gap in a superior surface of the shaft 36, in this example. The slot 52 extends through the superior surface of the shaft 36 to provide access to and from the passageway 50 via the slot 52.

Figure 4:
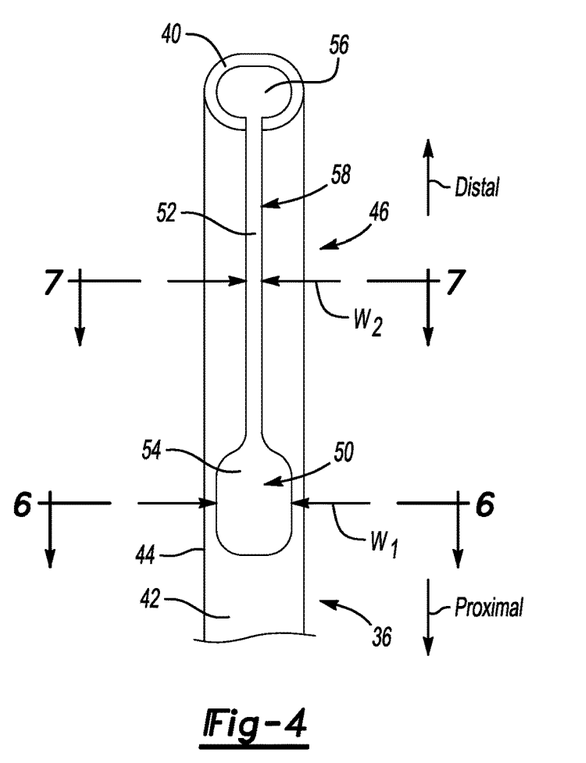
FIG. 4 is a superior view of a portion of the suture passer.
Figure 5:
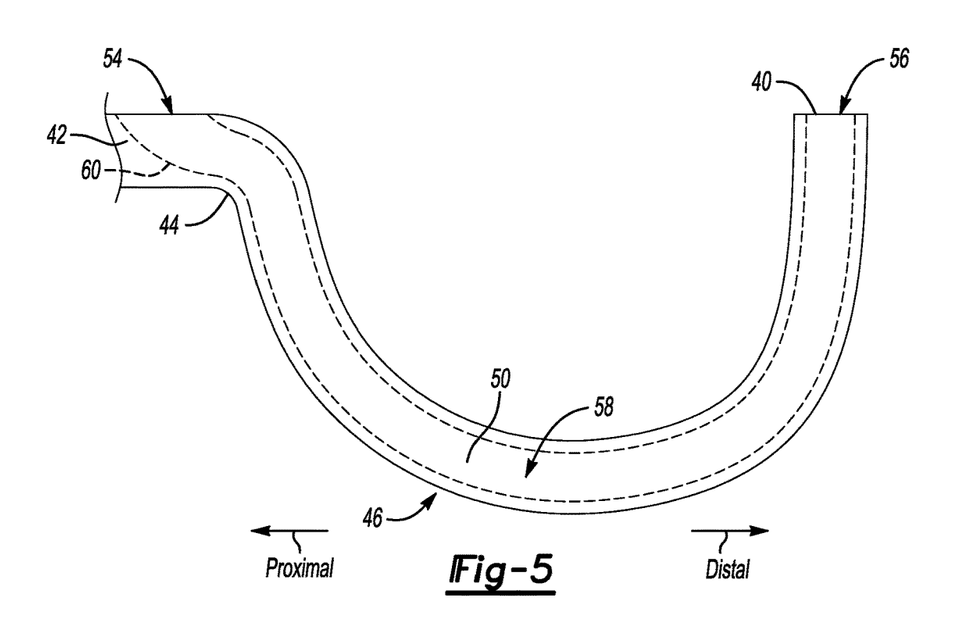
FIG. 5 is a side view of a portion of the suture passer.

With reference to FIGS. 4 and 5, the passageway 50 extends internally through the shaft 36 along a length from an entrance 54 adjacent the point 44 to an exit 56 adjacent the distal end 40. Between the entrance 54 and the exit 56, the passageway 50 extends along a main portion 58 which is bound on all sides by the shaft 36, with the exception of the slot 52, which, again, is provided by a gap in a superior surface of the shaft 36. The main portion 58 is the majority of the passageway 50 by length in this example.

The passageway 50 follows the contour of the shaft 36. In particular, within the curved section 46, the main portion 58 of the passageway 50 is curved in the same manner as the curved section 46, as shown in FIG. 5, which illustrates the passageway 50 in phantom. Further, adjacent the entrance 54, the passageway 50 may include an inferior wall 60 which gradually increases in depth to avoid sharp corners within the passageway 50.

Figure 6:
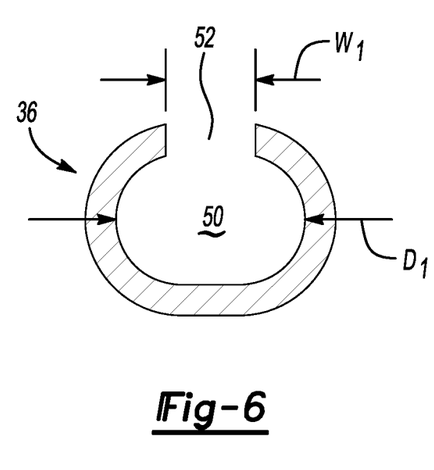
FIG. 6 is a cross-sectional view of the suture passer taken along line 6-6 in FIG. 4, and illustrates an example arrangement of a passageway and a slot adjacent an entrance of the passageway.
Figure 7:
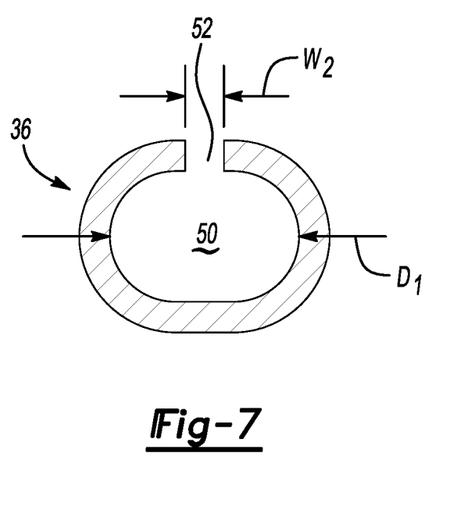
FIG. 7 is a cross-sectional view of the suture passer taken along line 7-7 in FIG. 4, and illustrates an example arrangement of the passageway and the slot adjacent a main portion of the passageway.

The slot 52 has a variable width along the length of the passageway 50. With reference to FIG. 4, the width of the slot 52 is measured in a side-to-side direction, such as a left-to-right direction, which is perpendicular to the central longitudinal axis A. In particular, with reference to FIGS. 4, 6, and 7, the slot 52 exhibits a first width $W_1$ adjacent the entrance 54 and a second width $W_2$ along the main portion 58 of the passageway 50. The first width $W_1$ is greater than the second width $W_2$. In particular, the first width $W_1$ is sized so permit the sheath 32 and the strand of suture 30 to enter the passageway 50 through the slot 52 adjacent the entrance 54. The second width $W_2$ is sized so as to prevent the sheath 32 from exiting the passageway 50 via the slot 52 but to permit the strand of suture 30 to exit the passageway 50 via the slot 52. In an example, the slot 52 exhibits the second width $W_2$ along the entirety of the main portion 58, and in particular along the entirety of the curved section 46 of the shaft 32 and at the distal end 40. The second width $W_2$ may gradually widen adjacent the distal end 40 in other examples. Adjacent the entrance 54, the slot 52 may gradually taper from the first width $W_1$ to the second width $W_2$.

The passageway 50 exhibits a diameter $D_1$ along substantially the entire length of the passageway 50. The diameter $D_1$ corresponds to a diameter $D_2$ (FIG. 3) of the sheath 32, and in particular the diameter $D_1$ is sized slightly larger than the diameter $D_2$ so as to allow the sheath 32 to slide within the passageway 50 from the entrance 54 to the exit 56.

Figure 3:
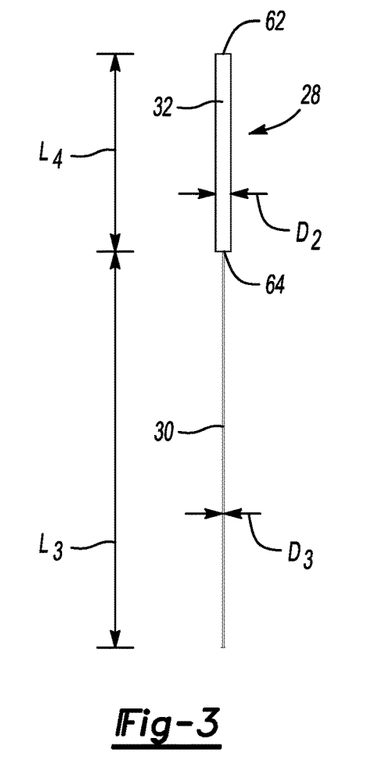
FIG. 3 illustrates an example assembly including a sheath and a strand of suture.

With reference to FIG. 3, the strand of suture 30 is a high strength braided suture, such as Arthrex, Inc.'s FiberTape™. The strand of suture 30 may include a multifilament cover formed of a plurality of braided fibers of ultrahigh molecular weight polyethylene (UHMWPE) and fibers of polyester. The cover may surround a core formed of twisted fibers of ultrahigh molecular weight polyethylene (UHMWPE). This disclosure is not limited to any particular type of suture, however.

Figure 10:
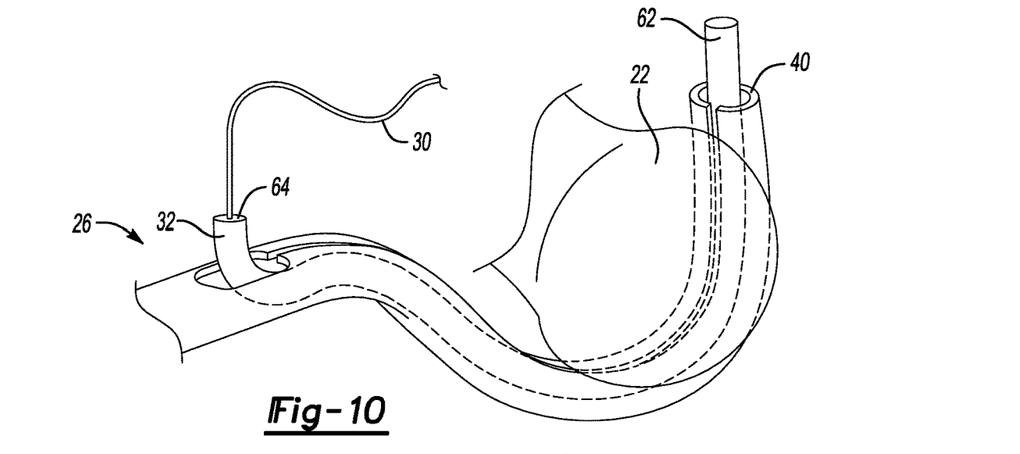
FIG. 10 is another view of the suture passer and assembly arranged relative to the bone, and in particular illustrates the sheath being pushed through the passageway of the suture passer.

Further, the strand of suture 30 exhibits a diameter $D_3$ less than the diameter $D_2$ of the sheath 32 and less than the width $W_2$ so as to permit the strand of suture 30 to exit the passageway 50 via the slot 52. The strand of suture 30 projects from the sheath 32 by a length $L_3$, which is greater than a length $L_4$ of the sheath 32. The length $L_4$ of the sheath 32 is greater than a length of the passageway 50 such that, when inserted into the passageway 50, a distal end 62 of the sheath 32 can project out of the exit 56 while a proximal end 64 of the sheath 32 is proximal to the entrance 54, as shown in FIG. 10, which increases the ease of passing the sheath 32 through the passageway 50. The length $L_3$ of the strand of suture 30 is such that the strand of suture 30 can be passed around a bone a plurality of times and manipulated in a desired manner, such as being tied into a knot. In this respect, the length $L_3$ may be many multiples of the length $L_4$, and FIG. 3 is not to scale in this regard.

The sheath 32, in this example, is more rigid than the strand of suture 30. In this way, a user can maneuver the sheath 32 more easily than the suture 30. In particular, it is easier for a user to insert the sheath 32 into the entrance 54 of the passageway 50 than the strand of suture 30. Further, it is easier for a user to retrieve the sheath 32 from the exit 56 of the passageway 50 than the strand of suture 30. In an example, the sheath 32 is made of a polymer material. The material of the sheath 32 may be considered semi-rigid, such that the sheath 32 is relatively stiff when compared to the strand of suture 30, but is not inflexible such that the sheath 32 can bend to conform with the shape of the curved section 46 as the sheath 32 moves through the curved section 46. The sheath 32 may be cylindrical, and may resemble a tube. The sheath 32 may be circular in cross-section, or may resemble another shape in cross-section. The sheath 32 may be either hollow or solid. The sheath 32 can be overmolded or attached to an end of the strand of suture 30 using another attachment technique.

Figure 8:
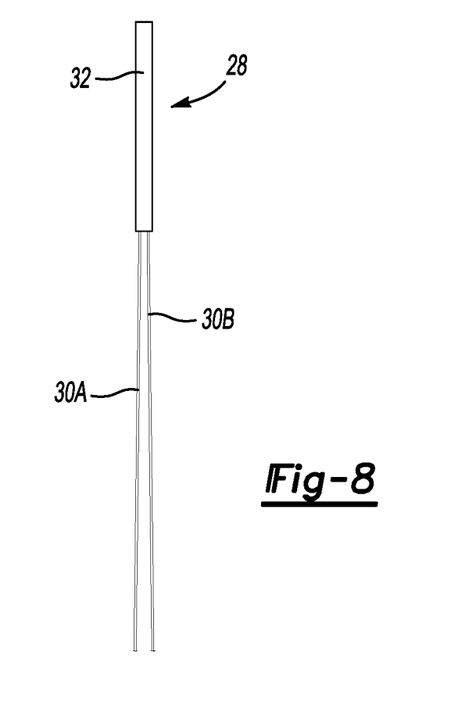
FIG. 8 illustrates another example assembly including a sheath and two strands of suture.

While in FIG. 3 only one strand of suture 30 projects from the sheath 32, additional strands of suture could project from the sheath 32. FIG. 8 is representative of another assembly 28 including two strands of suture 30A, 30B projecting from the sheath 32. Each strand of suture 30A, 30B is configured similar to the strand of suture 30. Additional strands of suture may project from the sheath 32 in other embodiments.

Figure 9:
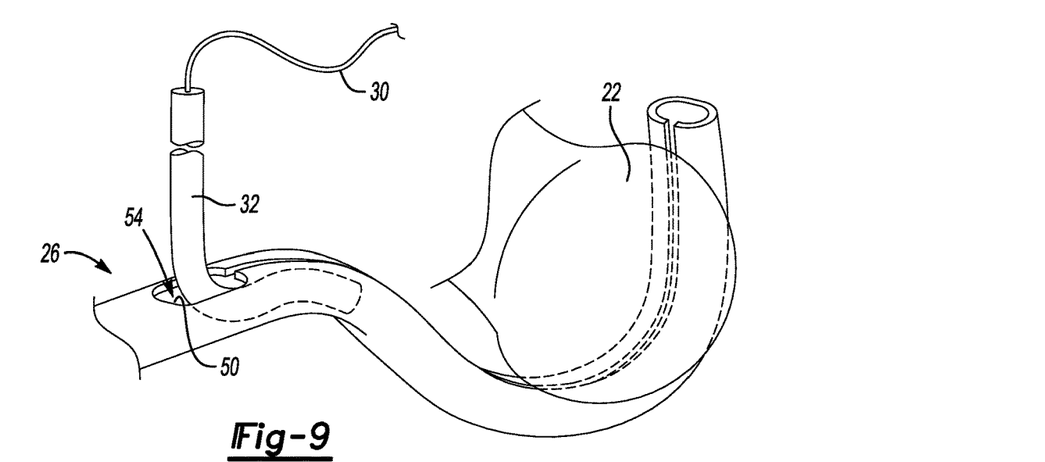
FIG. 9 is a view of a suture passer and an assembly arranged relative to bone, and in particular illustrates the sheath of the assembly being inserted into the entrance of the passageway of the suture passer.
Figure 11:
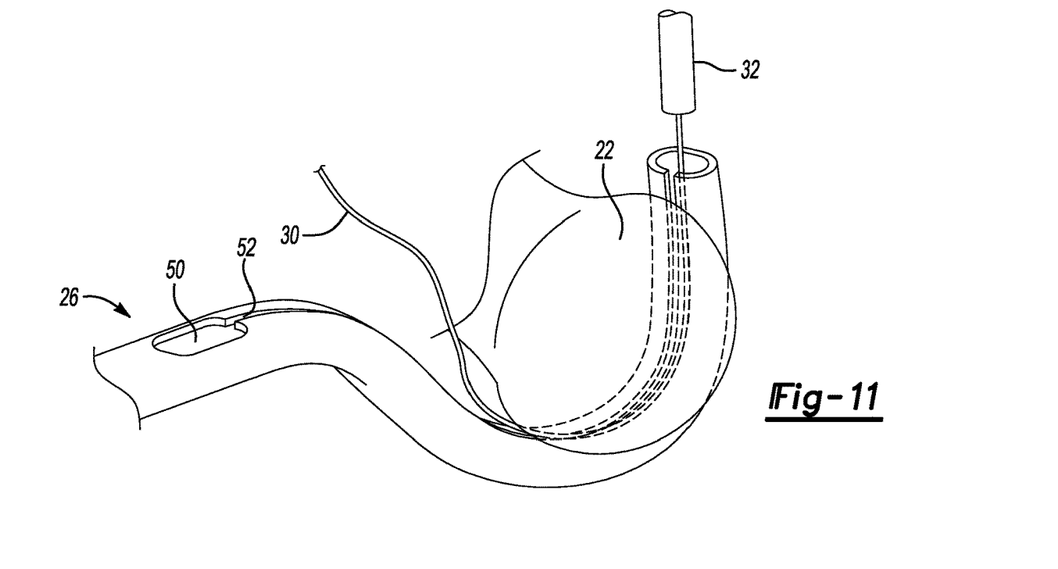

An example method of this disclosure will now be described with reference to FIGS. 9-11. With reference to FIG. 9, the suture passer 26 is positioned relative to a bone 22, which may be a femur, sternum, or humerus, as examples, adjacent a location where a bone cerclage is to be provided. As shown in FIG. 9, the curved section 46 of the shaft 36 is arranged such that the curved section 46 extends partially around the bone 22.

When the suture passer 26 is in position, the user passes the strand of suture 30 around the bone 22 by first inserting the sheath 32 into the entrance 54 of the passageway 50, as shown in FIG. 9. The user continues feeding the sheath 32 into the passageway 50 by pushing on the sheath 32, as shown in FIG. 10. In FIG. 10, a distal end 62 of the sheath 32 projects out of the passageway 50 and, in particular, projects from the distal end 40 of the suture passer 26. The user can then grasp, using a tool for example, the distal end 62 of the sheath 32 and pull the sheath 32 out of the passageway 50. In FIG. 11, the sheath 32 is fully removed from the passageway 50 and the strand of suture 30 has been passed around the bone 22. Next, the strand of suture 30 exits the passageway 50 via the slot 52. The strand of suture 30 can then be secured relative to the bone 22 or can be passed around the bone 22 one or more additional times.

If passing the strand of suture around the bone 22 again, the user may first reposition the suture passer 26. Because of the strand of suture 30 has exited the passageway 50 via the slot 52, the user does not need to fully remove the suture passer 26 from a surgical cavity to reposition the suture passer 26. Rather, in an example, the user can reposition the suture passer 26 by moving the suture passer 26 along a length of the bone 22, such as by sliding the suture passer 26 relative to the bone 22. Once repositioned, the user can pass the strand of suture 30 around the bone 22 again by repeating the aforementioned steps, namely those shown and described relative to FIGS. 9-11.

In an example method, the strand of suture 30 is passed around the bone 22 at least twice. When the strand of suture 30 has been passed around the bone 22 a desired number of times, the strand of suture is tensioned and secured to the bone to provide the suture wrap cerclage 20. The sheath 32 may be separated from the strand of suture 30 by cutting the strand of suture 30 adjacent the sheath 32.

The system of this disclosure may include one or more additional items. One such item is a suture tensioner, which is a device that allows the user to tension the strand of suture 30 suture to an appropriate level. An example of such a device is Arthrex's AR-1529 Suture Tensioner and Tensiometer. A suture tensioner is not required in all examples, but its use may increase the overall tightness of the suture wrap cerclage 20 relative to a hand-tensioned cerclage. Its use may further increase efficiency and repeatability relative to hand-tensioning.

The strand of suture 30 may be secured relative to the bone 22 by tying a knot, and without implanting any structure in the body, with the exception of the strand of suture 30. Other aspects of this disclosure, however, are "knotless," meaning the securing step includes securing the strand of suture 30 to the bone 22 without tying any knots. In an example, the strand of suture 30 is secured to the bone 22 using a knotless suture anchor, such as Arthrex's SwivelLock® or PushLock®. Various other structures, such as bone screws or bone plates may be used alone or in combination to secure the strand of suture 30 relative to the bone 22.

Figure 12:
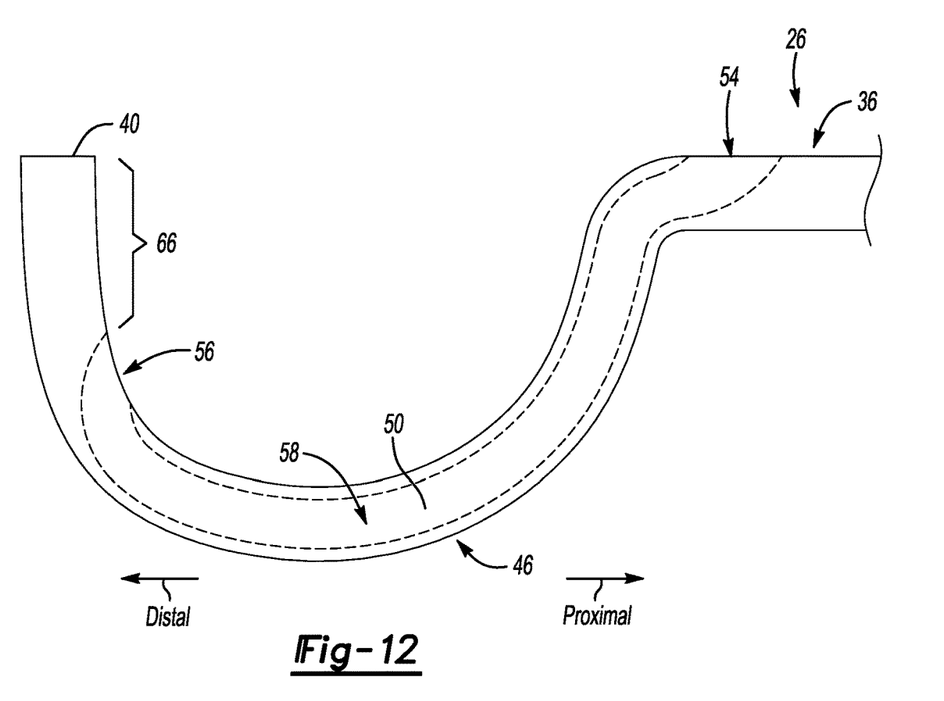
FIG. 12 is a side view of another embodiment of the suture passer in which a shaft of the suture passer includes a bendable section.
Figure 13:
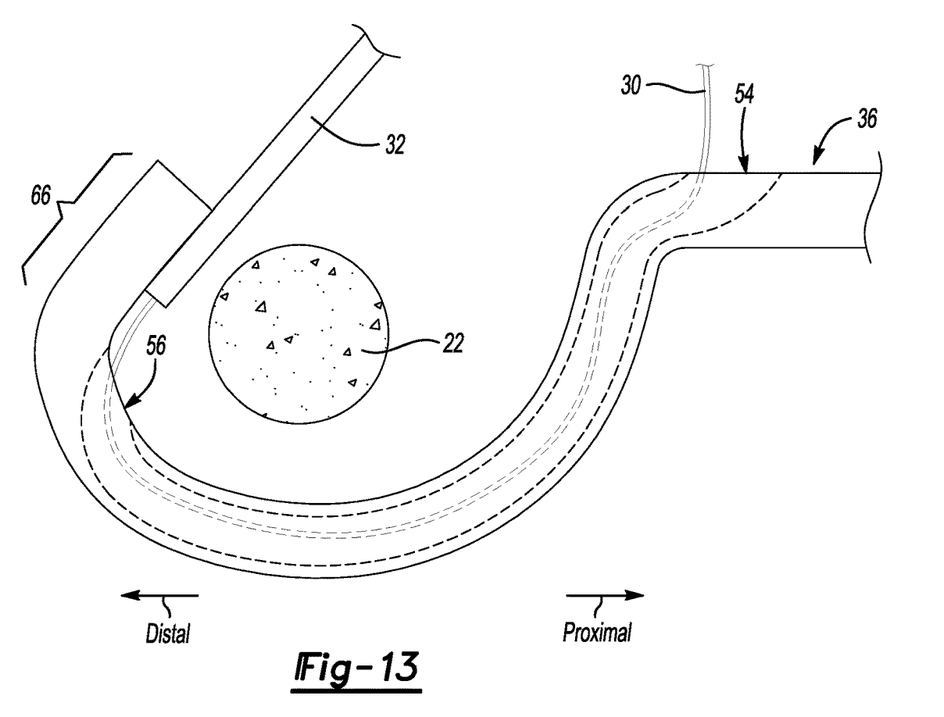

Another example embodiment of the suture passer 26 is illustrated relative to FIGS. 12 and 13. In this example, the suture passer 26 is configured similar to the above-described embodiments, with some exceptions, which will now be described. In the embodiment of FIGS. 12 and 13, the suture passer 26 is configured such that a portion of the curved section 46 of the shaft 36 is bendable to alter the effective size and/or shape of the curved section 46. In this way, the curved section 46 can be bent to more closely match the size and/or shape of a particular bone, which in turn reduces the likelihood that the suture passer 26 will contact and/or interfere with tissue adjacent the bone.

With reference to FIG. 12, the exit 56 of the passageway 50 is spaced-apart proximally from the distal end 40 of the shaft 36. In an example, the exit 56 is spaced-apart from the distal end 40 by an arc length of about 1 inch along the curved section 46. A section 66 of the shaft 36 between the exit 56 and the distal end 40 can be bent by a surgeon, for example, to adjust an effective size and/or shape of the curved section 46. Since the passageway 50 does not extend within the section 66, bending the section 66 does not impede the passage of suture 30 or the sheath 32 within the passageway 50.

In an example, the section 66 is integrally formed with the remainder of the shaft 36 and is made of the same material as the remainder of the shaft 36. An exemplary material of the shaft 36 and section 66 is a metallic material such a titanium. The material of the shaft 36 and section 66 is such that the section 66 holds a new, bent shape after the section 66 is bent to that new shape. The section 66 can be bent to accommodate the size of a particular bone or section of bone, used to pass suture around that bone, and then re-bent in a different manner to accommodate a differently-sized bone or bone section. For instance, the section 66 can be bent in a first direction, used to pass suture, and then later bent in a second, opposite direction and used to pass suture relative to another bone or bone section. The shaft 36 and section 66 may be made of different materials, in other examples. In those examples, the section 66 may be formed using an additive manufacturing technique.

FIG. 13 illustrates an example in which the section 66 has been bent such that the section 66 exhibits a new shape relative to its configuration in FIG. 12. The section 66 is bent by a surgeon, for example, before the shaft 36 is arranged relative to the bone 22 and before the suture 30 or sheath 32 are inserted into the passageway 50. In FIG. 13, the section 66 has been deflected proximally relative to its position in FIG. 12. Thus, the curved section 46 more closely follows the contour of the bone 22, which is relatively small in this example, than if the curved section 46 were not bent. In this way, unwanted interference between the shaft 36 and soft tissue adjacent the bone 22 is mitigated if not eliminated. The section 66 also serves to guide the sheath 32 around the bone 22 after the sheath 32 exits the exit 56, such that the sheath 32 can be readily retrieved by a surgeon.

The suture wrap cerclages of this disclosure provide a reliable and effective bone cerclage, which promotes healing of fractured bones. Further, the disclosed methods and systems allow surgeons to provide suture wrap cerclages in an efficient manner without sacrificing consistency or quality.

It should be understood that terms such as "proximal," "distal," "inferior," and "superior" are used consistent with their art-accepted meaning. These terms should not otherwise be considered limiting.

Although the different examples have the specific components shown in the illustrations, embodiments of this disclosure are not limited to those particular combinations. It is possible to use some of the components or features from one of the examples in combination with features or components from another one of the examples. In addition, the various figures accompanying this disclosure are not necessarily to scale, and some features may be exaggerated or minimized to show certain details of a particular component or arrangement.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A system for providing a bone cerclage, comprising:
a suture passer including a shaft, wherein the shaft includes a passageway and a slot leading to the passageway, wherein the passageway extends internally to the shaft between an entrance and an exit distal to the entrance, wherein the passageway includes a main portion between the entrance and the exit, wherein the slot includes a first width adjacent the entrance and a second width along the main portion, and wherein the first width is greater than the second width; and
a sheath and a strand of suture, wherein the strand of suture is attached to the sheath and projects from the sheath, wherein a length of the sheath is longer than a length of the passageway, and wherein the passageway is sized so as to allow the sheath to slide within the passageway from the entrance to the exit.

2. The system as recited in claim 1, wherein the sheath is more rigid than the strand of suture.

3. The system as recited in claim 1, wherein the sheath exhibits a larger diameter than the strand of suture.

4. The system as recited in claim 1, wherein the strand of suture is a first strand of suture and at least one additional strand of suture projects from the sheath.

5. The system as recited in claim 1, wherein:
the first width is sized so as to permit the sheath and suture to enter the passageway via the slot, and
the second width is sized so as to prevent the sheath from exiting the passageway via the slot and so as to permit suture to exit the passageway via the slot.

6. The system as recited in claim 1, wherein the slot is provided by a gap in a superior surface of the shaft.

7. The system as recited in claim 1, wherein:
the shaft includes a curved section, and
the passageway and slot are provided at least partially in the curved section.

8. The system as recited in claim 7, wherein:
the suture passer includes a handle connected to the shaft, and
the shaft includes a substantially straight section between the handle and the curved section.

9. The system as recited in claim 8, wherein an entrance to the passageway is provided in the substantially straight section and is spaced-apart proximally from a point at which the substantially straight section meets the curved section.

10. The system as recited in claim 1, wherein the sheath exhibits a substantially constant diameter along an entire length of the sheath.

11. The system as recited in claim 10, wherein the sheath is cylindrical.

12. The system as recited in claim 1, wherein an exit of the passageway is spaced-apart proximally from a distal end of the shaft.

13. The system as recited in claim 12, wherein the passageway does not extend within a section of the shaft between the exit of the passageway and the distal end of the shaft.

14. The system as recited in claim 13, wherein the section is made of a material different than a remainder of the shaft.

15. The system as recited in claim 1, wherein a distal end of the shaft is blunt.

16. The system as recited in claim 1, wherein an inferior wall of the passageway gradually increases in depth moving distally from the entrance such that, when the sheath comes into contact with the inferior wall, the inferior wall directs the sheath into the main portion of the passageway.

17. The system as recited in claim 1, wherein a distal end of the sheath is distal to the strand of suture.

18. The system as recited in claim 1, wherein the sheath is made of a polymer material.

19. The system as recited in claim 18, wherein the sheath is overmolded to an end of the strand of suture.

20. A system for providing a bone cerclage, comprising:
 a suture passer including a shaft, wherein the shaft includes a passageway and a slot leading to the passageway, wherein the slot has a variable width along a length of the passageway; and
 a sheath and a strand of suture, wherein the strand of suture is attached to the sheath and projects from the sheath, wherein a length of the sheath is longer than a length of the passageway, wherein an exit of the passageway is spaced-apart proximally from a distal end of the shaft, wherein the passageway does not extend within a section of the shaft between the exit of the passageway and the distal end of the shaft, and wherein the section of the shaft between the exit of the passageway and the distal end of the shaft is bendable such that the section holds a bent shape different from an original shape of the section.

* * * * *